United States Patent [19]

Coombs

[11] 4,386,457

[45] Jun. 7, 1983

[54] SURGICAL BLADE REMOVER-RECEPTACLE

[75] Inventor: Donald W. Coombs, 8191 E. Helen St., Tucson, Ariz. 85715

[73] Assignees: Donald W. Coombs; Frances M. Brimmer, both of Tucson; Daniel J. Anderson, Glendale, all of Ariz. ; a part interest

[21] Appl. No.: 266,520

[22] Filed: May 22, 1981

[51] Int. Cl.³ .............................................. B23P 19/02
[52] U.S. Cl. ....................................... 29/235; 29/270; 206/355; 206/359
[58] Field of Search .......................... 29/270, 278, 235; 81/3.1 B, 3.4, 3.44; 220/334; 206/349, 355, 356, 359, 360

[56] References Cited

U.S. PATENT DOCUMENTS

| | | | |
|---|---|---|---|
| 763,352 | 3/1903 | Barton | 81/3.44 |
| 930,796 | 5/1909 | Quackenbush | 81/3.44 |
| 3,949,872 | 4/1976 | Paudras | 220/334 |
| 4,106,620 | 8/1978 | Brimmer et al. | 206/359 |
| 4,168,777 | 9/1979 | Gaskell et al. | 206/359 |

Primary Examiner—James L. Jones, Jr.
Assistant Examiner—Steven P. Schad
Attorney, Agent, or Firm—Cahill, Sutton and Thomas

[57] ABSTRACT

A device for removing a surgical blade from a scalpel handle includes a housing having an aperture. A surgical blade attached to a boss of the handle is inserted into the aperture. The boss is pressed downward into a narrow notch in the wall surrounding the aperture so that the edges of the notch engage the shank of the blade, preventing it from being moved into the notch with the boss and separating the shank of the blade from the rear portion of the boss. Two spring loaded pinch members extend from within the aperture so that they can be pinched together by the fingers of a user and engage the opposed edges of the blade, preventing it from moving as the handle is pulled away from the blade, causing the boss to become disengaged from the blade and withdrawn from an elongated hole in the shank of the blade. When the pinch members are released, the blade falls to the bottom of the interior of the housing, which serves as a receptacle.

9 Claims, 8 Drawing Figures

SURGICAL BLADE REMOVER-RECEPTACLE

BACKGROUND OF THE INVENTION

1. Field of the Invention: p The invention relates to devices for safely removing surgical blades from scalpel handles.

2. Description of the Prior Art:

The typical commercially available surgical blade has a sharpened tip and cutting edge and a shank extending to the rear portion of the blade. An elongated aperture in the shank receives a mating elongated boss on the forward tip portion of a scalpel handle. The aperture of the blade has a widened rear portion and a narrow forward portion to facilitate engagement of an undercut groove portion of the boss with the narrow portion of the blade aperture after insertion of the boss into the widened rear portion of the aperture. When the boss is completely inserted within the blade aperture, the rear edge of the aperture snaps over the rear portion of the boss, locking the blade to the handle. To remove the blade from the handle, the rear edge of the blade must be lifted away from the boss to allow the handle to be drawn away from the blade so that the undercut portion of the boss becomes disengaged from the narrow portion of the blade aperture.

Hand removal of surgical blades from scalpel handles is time consuming and unsafe. Numerous devices have been proposed to accomplish rapid and safe removal of surgical blades from scalpel handles and for providing convenient receptacles for storing used blades. However, all of the known devices for removing surgical blades require an undue amount of effort, care, and concentration by the user, so the unsafe practice of removing surgical blades from handles by hand continues to be used. For example, U.S. Pat. No. 4,106,620 discloses, in FIGS. 6A and 6B, the use of a device including an internally mounted notched retaining device. The surgical blade and the boss portion of the handle are inserted into the device through a small hole. The handle is manipulated so that the rear end of the blade slips beneath outwardly projecting ears of the retaining device. The handle then is manipulated to lift the rear portion of the boss from the rear portion of the blade aperture and withdraw the boss from the blade aperture. A great deal of difficulty is experienced in slipping the rear portion of the blade beneath the ears of the retaining element because the rear edge of a common surgical blade abuts a widened portion of the handle. Therefore, the device of U.S. Pat. No. 4,106,620 is generally unsatisfactory.

An undue amount of care and attention also is required by a user to effectively and safely use the blade removing devices shown in U.S. Pat. Nos. 4,120,397; 4,180,162 and 4,168,777. The device shown in U.S. Pat. No. 4,168,777 requires that the scalpel handle be precisely aligned with the body of the blade removing/receiving device to ensure that the edge of the shank of the scalpel blade properly engages a flange which retains the blade as the scalpel handle is withdrawn. In the device of U.S. Pat. No. 4,120,396, the scalpel blade must be carefully aligned with the body of the blade removing/receiving device as the blade is inserted therein, and the orientation of the handle relative to the body of the blade removing/receiving device must be precisely varied and at the same time a member having extensions for separating the shank of the blade from the blade engaging boss must be depressed in order to cause the shank of the blade to engage a retaining member as the handle is withdrawn. In the device of U.S. Pat. No. 4,180,162, the scalpel must be deployed to insert the blade into the blade removing/receiving device until the tip of the blade is engaged between an internal boss and a rounded internal corner; then the handle is moved to the right so that the shank of the blade engages an internal blade disengaging projection which causes the rear edge of the shank to engage a retaining member as the scalpel handle is withdrawn. None of the above-mentioned surgical blade removing/receptacle devices have found widespread use.

SUMMARY OF THE INVENTION

Briefly described, and in accordance with one embodiment thereof, the invention provides a blade remover-receptacle device for easily, safely, and conveniently removing surgical blades having a boss engaging aperture therein from a blade engaging boss of a scalpel handle. In the described embodiment of the invention, the remover-receptacle includes a housing having a narrow slot. A pair of pinch members extend through the slot and are spring-loaded to be spaced apart on either side of a narrow boss-receiving notch in a wall of the housing surrounding the aperture. The pinch members extend beyond the aperture to allow them to be gripped and pressed toward each other. In use, the blade and part of the boss of a scalpel are inserted into the slot, so that most of the blade is in the interior of the housing, and a portion of the boss is positioned in the narrow boss-receiving notch. As the handle is deployed to force the boss further into the notch, the edges of the notch exclude or prevent the shank of the blade from entering the notch, thereby causing the rear portion of the shank to become separated from the rear portion of the boss. The pinch members are squeezed toward each other to engage the opposed edges of the shank of the blade, preventing movement of the blade. The handle then is drawn away from the housing, causing the boss to become disengaged from the blade. When the pinch members are released, the blade falls to the bottom of the interior of the housing, which serves as a receptacle for used blades. In the described embodiment of the invention, a portion of the housing is hingeably connected to the remainder of the housing to allow emptying of the blades from the interior of the housing. In the described embodiment of the invention, the pinch members each include a length of wood dowel capped by a vinyl cap that extends through the slot in the housing. The pinch members are separated in the housing by a separator member attached to the interior of the housing. An elastic band tends to pull the lower end portions of the respective pinch members together beneath the separator member to cause the upper portions of the pinch members to be spaced apart.

BRIEF DESCRIPTION OF THE DRAWINGS

FIG. 4 is a top view of the blade remover-receptacle of FIG. 1.

DESCRIPTION OF THE INVENTION

Figure 1:
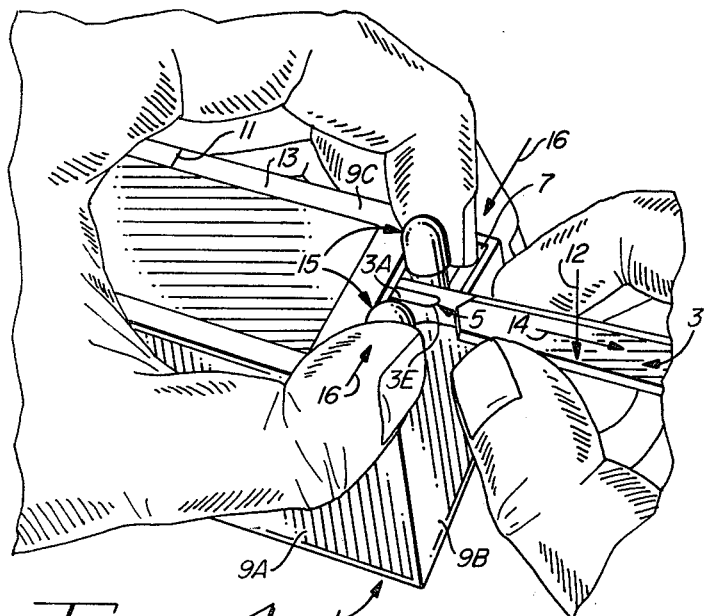
FIG. 1 is a perspective view illustrating use of the blade remover-receptacle of the present invention.

Referring now to the drawings, FIG. 1 shows the surgical blade remover-dispenser 1 being utilized to remove a surgical blade 5 from a scalpel handle 3. Remover-dispenser 1 includes a housing having a side wall 9A, a front wall 9B, a rear wall 9D (FIG. 3), a top 9C and a side wall 9E.

A rectangular aperture or slot 7 in the top front portion of remover-dispenser is bounded by the upper edges of walls 9A, 9B and 9E and is also bounded by an edge of top 9C. A narrow, elongated boss-receiving notch 21 is centrally disposed in the upper edge of front wall 9B. A pair of pinch members 15 extend from within the housing of remover-receptacle 1 on either side of notch 21 through a sufficient distance to enable the fingers of a user to engage pinch members 15 and squeeze them together to engage the opposite edges of the shank of a surgical blade 5, as shown in FIG. 1 and more fully explained hereinafter.

Figure 3:
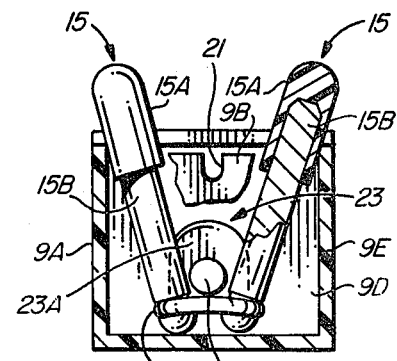
FIG. 3 is a partial section view taken along section line 3—3 of FIG. 2.

Pinch members 15 each include a post 15B and a sleeve or cap 15A. In the described embodiment of the invention, posts 15B are composed of sections of wooden dowel, and caps 15A are composed of vinyl. The lower portions of posts 15 are positioned on either side of a cylindrical separator member 23B. Cylindrical separator 23B is part of a metal device 23 having a horizontal portion 23C attached to the bottom of the interior of the housing or remover-separator 1 and a vertical portion 23A attached to horizontal portion 23C. Cylindrical separator 23B is attached to the upper portion of vertical member 23A and extends horizontally from vertical member 23A between the lower portions of posts 15B. An elastic band 17 is resiliently stretched to engage grooves 15C disposed at the lower end portions of each of posts 15B, thereby providing a spring-loading or bias which maintains the upper portion of pinch members 15 spaced apart, as shown in FIG. 3, by urging the lower end portions of posts 15B together, as also shown in FIG. 3. When caps 15A are squeezed together, the presence of separator 23B causes elastic band 17 to be stretched, as shown in FIG. 3.

Figure 2:
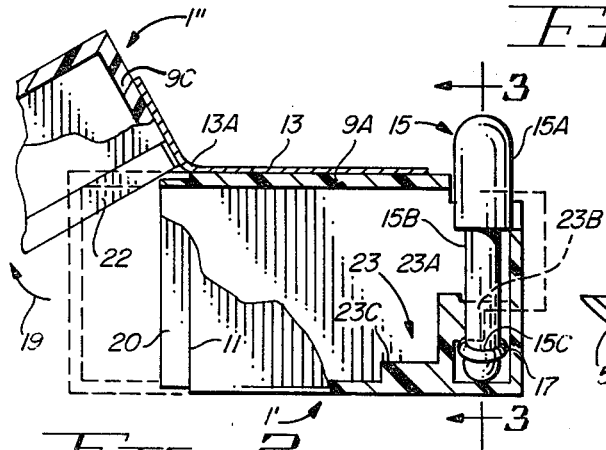
FIG. 2 is a partial cutaway section view of the blade remover-receptacle shown in FIG. 1.

As best seen in FIGS. 2 and 4, the housing of surgical blade remover-receptacle 1 includes a front portion 1' and a rear portion 1" that is hingeably connected along its top surface 9C by means of a hinge 13. Arrow 19 in FIG. 2 illustrates how rear portion 1" can be opened, allowing surgical blades which have been removed and stored in the housing can be emptied out of the housing. In one embodiment of the invention, the entire housing is composed of plastic, and hinge 13 is simply a flexible label that is adhesively attached to top surface 9C and extends on either side of joint 11 between sections 1' and 1". As shown in FIG. 2, the joining portions of front section 1' and rear section 1" include overlapping portions 20 and 22 that fit together closely and overlap when the housing is closed.

Figure 8:
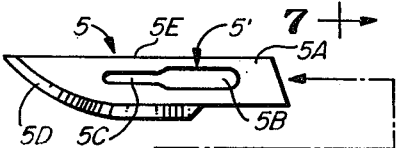
FIG. 8 is a drawing illustrating the details of a surgical blade and a blade engaging boss of a scalpel handle.

Use of the remover-receptacle 1 will be best explained after the structure of a typical surgical blade 5 and a scalpel handle 3 are understood precisely. Referring to FIG. 8, surgical blade 5 has a cutting edge 5D, a top edge 5E, and a shank 5A, a boss-engaging aperture 5' including a narrow front portion 5C and a wide and rear portion 5B. Scalpel handle 3 includes a blade-engaging boss 3A that includes an undercut groove 3B, indicated by dotted lines, that extends from a point 3C on either side of boss 3A along the sides and leading tip of boss 3A. When blade 5 is properly attached to scalpel handle 3, boss 3A is inserted into the widened rear portion 5B of aperture 5', and the narrow forward portion 5C of aperture 5' slides into the groove 3B. A rear edge 3E of boss 3A snaps through the rear portion of enlarged portion 5B of aperture 5' when boss 3A has slid as far forward as possible in narrow portion 5C of aperture 5'.

Figure 5:
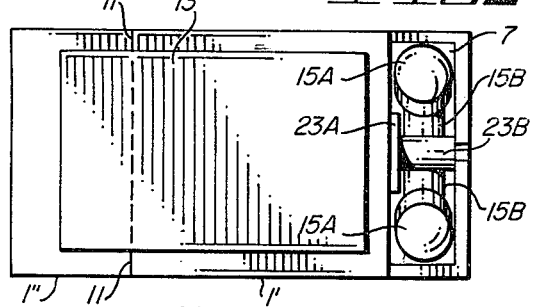
FIG. 5 is a partial top view drawing useful in explaining the operation of the blade remover-receptacle.
Figure 7:
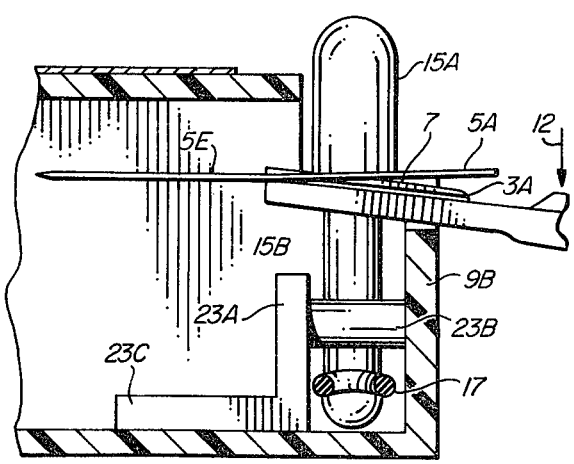
FIG. 7 is a partial section view taken along section line 7—7 of FIG. 6.

To remove blade 5 from handle 3, the user first inserts the leading tip of blade 5 into rectangular opening 7, as indicated in FIG. 5, so that the forward portion of blade 5, indicated by dotted lines 5" in FIG. 5 extends beneath top 9C of the housing. The narrow boss 3A is pushed downward into boss receiving notch 21 by pushing handle 3 downward in a direction indicated by arrow 12 in FIGS. 1 and 7. Boss 3A then is separated from the shank 5A of blade 5 because the shank 5A is wider than notch 21. This separator in FIG. 7.

The user then can use a thumb and index finger to engage the caps 15A of pinch members 15 and squeeze them together, as indicated in FIG. 1 by arrows 16, so that pinch members 15 engage edges 5D and 5E of blade 5, preventing it from moving. The user then pulls scalpel handle 3 away from remover-receptacle 1 in the direction indicated by arrow 14 in FIG. 1. Boss 3A then moves clear of the rear edge of blade aperture 5', and groove 3B becomes disengaged from narrowed aperture portion 5C of blade 5 as the handle is removed. The user then simply releases pinch members 15, and blade 5 drops to the bottom of the interior of retainer-receptacle 1. When a sufficient number of used blades have been removed and released in the manner described above, rear portion 1" can be opened to empty the housing.

Figure 6:
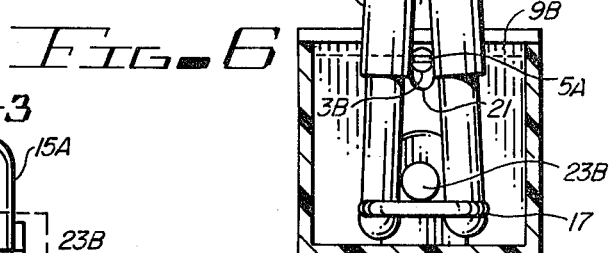
FIG. 6 is a partial section view similar to FIG. 3 and is useful in explaining the operation of the invention.

The vinyl caps 15A can engage the opposite edges of the shank 5A of blade 5, as indicated in FIG. 6, in which case the resilient material of which caps 15A are composed, yields somewhat to accomplish effective gripping of the edges of the shanks 5A of blade 5. However, effective operation also will result if caps 15A are shorter so that posts 15B engage the opposite edges of shank 5A.

The described device is very economical to manufacture, since the housing can be implemented by means of a Model 531 standard plastic box made by AMAC Plastic Products Corporation, of Sausilito, Calif. The box can be easily modified to provide aperture 7, install retaining element 23, and provide boss engaging notch 21 and hinge label 13.

While the invention has been described with reference to a particular embodiment thereof, those skiller in the art will be able to provide numerous other box configurations and pincher element configurations which manipulate to grip opposed edges of the shank of the surgical blade without departing from the true spirit and scope of the invention. For example, a pinch mechanism could be mounted adjacent to the outer surface of wall 9B instead of the inner wall, and slot 7 could be made substantially narrower than indicated in the drawings. Furthermore, the pinch members 15 could be modified such that they are entirely internal to the housing, and the button-like mechanism on the adjacent opposed sides of the housing could be provided, although at additional expense, to urge the pinch members together to engage the shank of the blade by squeezing the adjacent opposed sides of the housing toward each other.

I claim:

1. A device for removing surgical blades from a handle, said handle including a narrow-blade-engaging boss, the boss having a groove portion for engaging a narrowed forward portion of a boss-engaging aperture of said blade, said boss-engaging aperture also having a widened rear portion, said blade having a shank with two opposed edges, said device comprising in combination:

(a) a housing, said housing having therein an aperture for receiving said blade and a portion of said boss when said blade is attached to said boss;
   (b) a boss receiving notch for receiving a portion of the boss, and first and second shoulders adjacent to said boss receiving notch for engaging said shank of said blade to cause separation of a rear portion of said shank for said boss as a portion of said boss is forced into said boss-receiving notch; and
   (c) blade gripping means attached to said housing adjacent to said boss receiving notch for gripping said opposed side edges of said shank to retain said blade in place while said handle is disengaged from said blade by pulling said handle away from said blade while said separation of said rear portion of said shank from said boss is maintained, said blade gripping means being manually actuable to grip said opposed side edges of said blade and manually releasable to disengage said opposed side edges of said blade to thereby release said blade after said handle has been removed from said blade, said blade gripping means being located so that the released blade falls into the interior of said housing, said blade gripping means including first and second post elements which can be manually urged together to engage said opposed side edges of said shank to thereby grip said shank, said first and second post elements being connected to means for elastically biasing said first and second post elements apart.

2. The device of claim 1 wherein said blade gripping means is attached to said housing within said housing, a respective portion of each of said post elements extending through said aperture of said housing.

3. The device of claim 2 wherein said boss receiving notch is disposed in a wall of said housing adjacent to said aperture of said housing, said boss receiving notch being sufficiently wide to receive said boss but not sufficiently wide to receive said shank of said blade when said blade is attached to said boss.

4. The device of claim 3 wherein said first and second post members have upper portions extending through said aperture of said housing, said first and second posts engaging said opposed side edges of said shank when said upper portions of said first and second posts members are squeezed toward each other.

5. The device of claim 4 wherein an upper portion of each of said first and second post members is composed of resilient plastic material to improve engagement with said opposed edges of said shank.

6. The device of claim 4 including a separator element attached to said housing and extending between the lower portions of said first and second post members and elastic means connected between the lower portions of said first and second post means beneath said separator means to elastically bias the lower portion of said blade engaging means to tend to maintain the upper portions of said first and second post members apart.

7. The device of claim 4 wherein said housing is composed of plastic.

8. The device of claim 7 wherein said housing is rectangular, and has first and second portions and means for hingeably connecting said first and second portions to allow opening of said housing to facilitate emptying of used blades therefrom.

9. The device of claim 8 wherein said hinge means includes a label adhesively attached to the top of said housing.

* * * * *